(12) United States Patent
Matsui et al.

(10) Patent No.: US 6,414,012 B1
(45) Date of Patent: Jul. 2, 2002

(54) HETEROCYCLIC DERIVATIVES, METHOD OF PRODUCTION THEREOF AND PHARMACEUTICAL USE THEREOF

(75) Inventors: Hiroshi Matsui, Nara; Shoji Kamiya, Kyoto; Hiroaki Shirahase, Nagaokakyo; Shohei Nakamura, Kyoto; Katsuo Wada, Takatsuki, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/373,163

(22) Filed: Aug. 12, 1999

Related U.S. Application Data

(62) Division of application No. 08/809,242, filed as application No. PCT/JP95/01873 on Sep. 20, 1995, now Pat. No. 5,990,150.

(30) Foreign Application Priority Data

Sep. 20, 1994 (JP) .............................. 6-225166

(51) Int. Cl.$^7$ ......................... A61P 9/10; A61K 31/404
(52) U.S. Cl. ..................... 514/415; 514/824; 514/866
(58) Field of Search .................. 514/415, 235.2, 514/253, 254, 311, 314, 323, 339, 397, 414, 80, 82, 186, 187, 824, 866, 416

(56) References Cited

U.S. PATENT DOCUMENTS

| | | |
|---|---|---|
| 3,824,230 A | 7/1974 | Hester, Jr. |
| 4,615,966 A | 10/1986 | Borror et al. |
| 5,143,919 A | 9/1992 | Meguro et al. |
| 5,219,859 A | 6/1993 | Festal et al. ............ 514/269 |
| 5,254,590 A | 10/1993 | Malen et al. |
| 5,254,919 A | 10/1993 | Malen et al. |
| 5,256,782 A | 10/1993 | Meguro et al. |
| 5,990,150 A | 11/1999 | Matsui et al. |
| 6,127,403 A | 10/2000 | Matsui et al. |

FOREIGN PATENT DOCUMENTS

| | | |
|---|---|---|
| EP | 0 354 994 | 2/1990 |
| EP | 0 375 133 | 6/1990 |
| EP | 0 427 860 | 5/1991 |
| EP | 0 512 570 | 11/1992 |
| GB | 991937 | 5/1965 |
| JP | 117651/1990 | 5/1990 |
| JP | 7259/1991 | 1/1991 |
| JP | 04066568 | * 3/1992 |
| JP | 66568/1992 | 3/1992 |
| JP | 05 097802 | 4/1993 |
| JP | 05 140102 | 6/1993 |
| WO | 91/09017 | 6/1991 |
| WO | 92/18462 | 10/1992 |
| WO | WO 94/14801 | 7/1994 |
| WO | WO 97/12860 | 4/1997 |

OTHER PUBLICATIONS

De Vries et al., "Potential Antiatherosclerotic Agents. 5.$^1$ An Acyl–CoA: Cholesterol O–Acyltransferase Inhibitor with Hypocholesterolemic Activity", *J. Med. Chem.*, 29, pp. 1131–1133 (1986).
Patent Abstracts of Japan: JP 04 066568 (Mar. 2, 1992).
Miyamoto et al., "Antioxidants Protect Against Glutamate–Induced Cytotoxicity in a Neuronal Cell Line," *The Journal of Pharmacology and Experimental Therapeutics*, 250 (3), 1132–1140 (1989).
Murphy et al., "Glutamate Toxicity in a Neuronal Cell Line Involves Inhibition of Cystine Transport Leading to Oxidative Stress," *Neuron*, 2 1547–1558 (Jun. 1989).
Mazza et al., "N–Acylindolines with Phytotoxic Activity," II Farmaco Edizione Scientifica, 32 (1), 54–66 (1977).
Cram et al., *Organic Chemistry*, $2^{nd}$ Edition, McGraw–Hill Book Company, New York, pp. 76–77, 255, 304–305, 361–362 (1964).
Mitsui Petrochem Ind Ltd, "Preparation of 1–Actl–5–Bromoindoline,"Patent Abstracts of Japan, 31 (4) (JP 54 084572) (Sep. 4, 1979).

\* cited by examiner

*Primary Examiner*—Edward J. Webman
*Assistant Examiner*—Helen Nguyen
(74) *Attorney, Agent, or Firm*—Leydig, Voit & Mayer, Ltd.

(57) ABSTRACT

Heterocyclic derivatives of the formula (I)

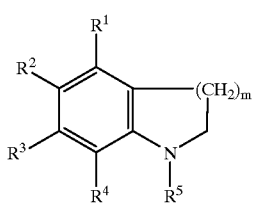

(I)

wherein each symbol is as defined in the specification, pharmaceutically acceptable salts thereof and method of producing them. Pharmaceutical compositions containing the heterocyclic derivative or a pharmaceutically acceptable salt thereof, particularly, ACAT inhibitors and lipoperoxidation inhibitors. The heterocyclic derivatives and pharmaceutically acceptable salts thereof of the present invention show superior ACAT inhibitory activity and lipoperoxidation inhibitory activity, and are useful as ACAT inhibitors and hyperlipemia inhibitors. To be specific, they are useful for the prevention and treatment of arteriosclerotic lesions of arteriosclerosis, hyperlipemia and diabetes, as well as ischemic diseases of brain, heart and the like.

2 Claims, No Drawings

HETEROCYCLIC DERIVATIVES, METHOD OF PRODUCTION THEREOF AND PHARMACEUTICAL USE THEREOF

This application is a division of application Ser. No. 08/809,242 filed Mar. 19, 1997 now U.S. Pat. No. 5,990,150.

TECHNICAL FIELD

The present invention relates to novel heterocyclic derivatives, a method of production thereof and pharmaceutical use thereof. More particularly, the present invention relates to novel heterocyclic derivatives having an indoline ring or tetrahydroquinoline ring, a method of production thereof and pharmaceutical use thereof, specifically acyl-CoA:cholesterol acyltransferase (hereinafter ACAT) inhibitors and lipoperoxidation inhibitors.

BACKGROUND ART

It is a well-known fact that arteriosclerosis is an extremely important factor causing various circulatory diseases, and active studies have been undertaken in an attempt to achieve suppression of the evolution of arterial sclerosis or regression thereof. In particular, although the usefulness of a pharmaceutical agent which reduces cholesterol in blood or arterial walls has been acknowledged, an ideal pharmaceutical agent exhibiting positive clinical effects while causing less side-effects has not been realized.

In recent years, it has been clarified that cholesterol accumulated in arterial walls in the ester form thereof significantly evolves arteriosclerosis. A decrease in cholesterol level in blood leads to the reduction of accumulation of cholesterol ester in arterial walls, and is effective for the suppression of evolution of arteriosclerosis and regression thereof.

Cholesterol in food is esterified in mucous membrane of small intestine, and taken into blood as chylomicron. ACAT is known to play an important role in the generation of cholesterol ester in mucous membrane of small intestine. Thus, if esterification of cholesterol can be suppressed by inhibiting ACAT in mucous membrane of small intestine, absorption of cholesterol by mucous membrane and into blood can be presumably prevented to ultimately result in lower cholesterol level in blood.

In arterial walls, ACAT esterifies cholesterol and causes accumulation of cholesterol ester. Inhibition of ACAT in arterial walls is expected to effectively suppress accumulation of cholesterol ester.

From the foregoing, it is concluded that an ACAT inhibitor will make an effective pharmaceutical agent for hyperlipemia and arteriosclerosis, as a result of suppression of absorption of cholesterol in small intestine and accumulation of cholesterol in arterial walls.

Conventionally, for example, there have been reported, as such ACAT inhibitors, amide and urea derivatives [J. Med. Chem., 29: 1131 (1986), Japanese Patent Unexamined Publication Nos. 117651/1990, 7259/1991, 32666/1993 and 327564/1992].

However, creation and pharmacological studies of these compounds have been far from sufficient.

Meanwhile, peroxidation of low density lipoprotein (LDL) is also highly responsible for accumulation of cholesterol ester in arterial walls. In addition, it is known that peroxidation of lipids in a living body is deeply concerned with the onset of arteriosclerosis and cerebrovascular and cardiovascular ischemic diseases.

Accordingly, a compound having both ACAT inhibitory activity and lipoperoxidation inhibitory activity is highly useful as a pharmaceutical product, since it effectively reduces accumulation of cholesterol ester in arterial walls and inhibits lipoperoxidation in the living body, thereby preventing and treating various vascular diseases caused thereby.

It is therefore an object of the present invention to provide a compound having ACAT inhibitory activity and lipoperoxidation inhibitory activity, a method for production thereof and pharmaceutical use thereof, particularly as an ACAT inhibitor and lipoperoxidation inhibitor.

DISCLOSURE OF THE INVENTION

The present inventors have conducted intensive studies with the aim of accomplishing the above-mentioned object and found that a certain heterocyclic derivative having an indoline ring or tetrahydroquinoline ring has lipoperoxidation inhibitory activity in addition to strong ACAT inhibitory activity, and that said compound has strong anti-hyperlipemia effect and anti-arteriosclerosis effect, which resulted in the completion of the invention.

Thus, the present invention relates to a heterocyclic derivative of the formula (I)

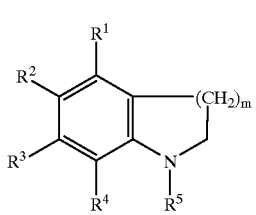

(I)

wherein
one of $R^1$, $R^2$, $R^3$ and $R^4$ is a group of the formula —NHCO—$R^6$ wherein $R^6$ is optionally substituted alkyl, optionally substituted cycloalkyl, optionally substituted cycloalkylalkyl, optionally substituted aryl, optionally substituted arylalkyl, optionally substituted heterocycle, optionally substituted heterocyclic alkyl, —$R^A SO_3 A$, —$R^B PO_3 B$ where $R^A$ and $R^B$ are each alkylene and A and B are each alkali metal or hydrogen atom, —$NR^7 R_8$ where $R^7$ is optionally substituted alkyl, optionally substituted cycloalkyl, optionally substituted cycloalkylalkyl, optionally substituted aryl or optionally substituted arylalkyl and $R^8$ is hydrogen atom or lower alkyl, or —$R^9$—$OCOR^{10}$ where $R^9$ is alkylene and $R^{10}$ is optionally substituted alkyl, optionally substituted heterocycle or optionally substituted heterocyclic alkyl, and the remaining three may be the same or different and each is independently a hydrogen atom, a lower alkyl or a lower alkoxy;

$R^5$ is an optionally substituted alkyl, an optionally substituted cycloalkyl, an optionally substituted cycloalkylalkyl, an optionally substituted aryl, an optionally substituted arylalkyl, an optionally substituted heterocycle, an optionally substituted heterocyclic alkyl, an alkenyl, an alkynyl, a dialkylaminoacyloxyalkyl, —$R^D SO_3 D$ or —$R^E PO_3 E$ where $R^D$ and $R^E$ are each alkylene and D and E are each alkali metal or hydrogen atom, provided that when $R^4$ is —NHCO—$R^6$, $R^5$ and $R^6$ optionally combinedly form a ring; and m is 1 or 2,

[hereinafter this compound is also referred to as Compound (I)] and a pharmaceutically acceptable salt thereof.

The present invention also relates to a method for producing the above-mentioned heterocyclic derivative or a pharmaceutically acceptable salt thereof, which comprises a step of ① reacting an amine of the formula (II)

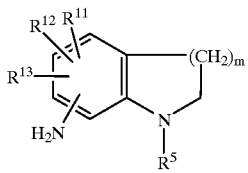
(II)

wherein $R_{11}$, $R_{12}$ and $R^{13}$ may be the same or different and each is independently hydrogen atom, lower alkyl or lower alkoxy, and $R^5$ and m are as defined above [hereinafter also referred to as Compound (II)], and an isocyanate of the formula (III)

$R^7$ NCO (III)

wherein $R^7$ is as defined above [hereinafter also referred to as Compound (III);

② reacting Compound (II) and a halogen compound of the formula (IV)

$R^6$ COX (IV)

wherein X is halogen atom and $R^6$ is as defined above [hereinafter also referred to as Compound (IV)];

③ reacting Compound (II) and a carboxylic acid of the formula (V)

$R^{6'}$ COOH (V)

wherein $R^{6'}$ is optionally substituted alkyl, optionally substituted cycloalkyl, optionally substituted cycloalkylalkyl, optionally substituted aryl, optionally substituted arylalkyl, optionally substituted heterocycle or optionally substituted heterocyclic alkyl [hereinafter also referred to as Compound (V)] or a reactive derivative thereof;

④ reacting an isocyanate of the formula (VI)

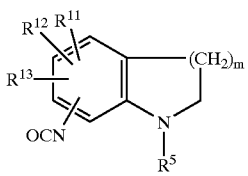
(VI)

wherein $R^5$, $R^{11}$, $R^{12}$, $R^{13}$ and m are as defined above [hereinafter also referred to as Compound (VI)], and an amine of the formula (VII)

$HNR^7 R^8$ (vii)

wherein $R^7$ and $R^8$ are as defined above [hereinafter also referred to as Compound (VII)]; or ⑤ reacting a compound of the formula (VIII)

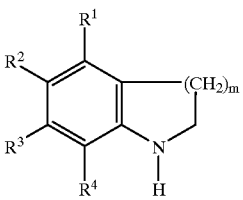
(VIII)

wherein $R^1$, $R^2$, $R^3$, $R^4$ and m are as defined above [hereinafter also referred to as Compound (VIII)], and a compound of the formula (IX)

$R^5$ X (IX)

wherein $R^5$ and X are as defined above [hereinafter also referred to as Compound (IX)].

The present invention also relates to pharmaceutical compositions, ACAT inhibitors and lipoperoxidation inhibitors containing the above-mentioned heterocyclic derivative or a pharmaceutically acceptable salt thereof.

In the present specification, each symbol denotes the following.

Lower alkyl at $R^1$, $R^2$, $R^3$, $R^4$, $R^8$, $R^{11}$, $R^{12}$ and $R^{13}$ may be linear or branched and preferably has 1 to 4 carbon atoms. Examples thereof include methyl, ethyl, propyl, isopropyl, butyl, isobutyl, sec-butyl, tert-butyl and the like.

Lower alkoxy at $R^5$, $R^2$, $R^3$, $R^4$, $R^{11}$, $R^{12}$ and $R^{13}$ may be linear or branched and preferably has 1 to 4 carbon atoms. Examples thereof include methoxy, ethoxy, propoxy, isopropoxy, butoxy, isobutoxy, sec- butoxy, tert-butoxy and the like.

Alkyl at $R^5$, $R^6$, $R^{6'}$, $R^7$ and $R^{10}$ may be linear or branched and preferably has 1 to 12 carbon atoms. Examples thereof include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, 1,1-dimethylpropyl, 1,1-dimethylbutyl, 1,1-dimethylpentyl, 1,1-dimethylhexyl, 3,3-dimethylbutyl, 4,4-dimethylbutyl and the like.

Cycloalkyl at $R^5$, $R^6$, $R^{6'}$ and $R^7$ preferably has 3 to 6 carbon atoms. Examples thereof include cyclopropyl, cyclobutyl, cyclopentyl, cyclohexyl and the like.

With regard to cycloalkylalkyl at $R^5$, $R^6$, $R^{6'}$ and $R^7$, its cycloalkyl moiety preferably has 3 to 6 carbon atoms and alkyl moiety preferably has 1 to 3 carbon atoms. Examples of cycloalkylalkyl include cyclopropylmethyl, cyclobutylmethyl, cyclopentylmethyl, cyclohexylmethyl, cyclopropylethyl, cyclopropylpropyl and the like.

Examples of aryl at $R^5$, $R^6$, $R^{6'}$ and $R^7$ include phenyl, naphthyl and the like.

Arylalkyl at $R^5$, $R^6$, $R^{6'}$ and $R^7$ has an aryl moiety as exemplified above and its alkyl moiety preferably has 1 to 4 carbon atoms. Examples of arylalkyl include benzyl, 1-phenylethyl, 2-phenylethyl, 1-phenylpropyl, 2-phenylpropyl, 3-phenylpropyl and the like.

Heterocycle group at $R^5$, $R^6$, $R^{6'}$ and $R^{10}$ is a monovalent group which occurs as a result of liberation of one hydrogen atom bonded to the ring of heterocyclic compound and may be aliphatic or aromatic. Examples thereof include pyrrolidinyl, piperidyl, piperidino, morpholinyl, morpholino, piperazinyl, pyrrolyl, imidazolyl, pyridyl and the like.

Heterocyclic alkyl at $R^5$, $R^6$, $R^6$ and $R^{10}$ has a heterocyclic moiety as exemplified above and its alkyl moiety preferably has 1 to 8 carbon atoms. Examples thereof include (1-pyrrolidinyl)butyl, morpholinopropyl, 1,1-dimethyl-2-(1-pyrrolidinyl)ethyl, 1,1-dimethyl-2-piperidinoethyl, 1,1-dimethyl-3-(imidazol-1-yl)propyl, (2,6-dimethylpiperidino)methyl, (2,6-dimethylpiperidino)ethyl, (2,6-dimethylpiperidino)propyl and the like.

The above-mentioned alkyl, cycloalkyl, cycloalkylalkyl, aryl, arylalkyl, heterocycle and heterocyclic alkyl may be substituted. Examples of the substituent include alkyl, amino, hydroxy, dialkylamino, aminoalkyl, alkoxy, carboxyl, alkoxycarbonyl, carboxyalkyl, acyloxy, phenyl, phenoxy, halogen atom and the like.

Alkyl in alkyl, dialkylamino, aminoalkyl and carboxyalkyl is exemplified by the above-mentioned lower alkyl. Alkoxy in alkoxy and alkoxycarbonyl is exemplified by the above-mentioned lower alkoxy. Acyloxy may be linear or branched and preferably has 2 to 5 carbon atoms. Examples thereof include acetyloxy, propionyloxy, butyryloxy, valeryloxy, pivaloyloxy and the like. Halogen atom is exemplified by those to be mentioned later. Alkyl in dialkylamino may be substituted by phenyl.

Alkenyl at $R_5$ may be linear or branched and preferably has 2 to 8 carbon atoms. Examples thereof include ethenyl, propenyl, isopropenyl, butenyl, pentenyl, hexenyl, heptenyl, octenyl, 3,3-dimethyl-2-propenyl and the like.

Alkynyl at $R^5$ may be linear or branched and preferably has 2 to 8 carbon atoms. Examples thereof include ethynyl, propynyl, butynyl, pentynyl, hexynyl, heptynyl, octynyl, 3,3-dimethyl-2-propynyl and the like.

Alkyl moiety of dialkylaminoacyloxyalkyl at $R^5$ preferably has 1 to 8 carbon atoms, and its acyl moiety may be linear or branched and preferably has 2 to 5 carbon atoms. Examples thereof include acetyl, propionyl, butyryl, valeryl, pivaloyl and the like. The dialkylaminoacyloxyalkyl is specifically exemplified by N,N-dimethylaminoacetoxyethyl, N,N-dimethylaminoacetoxypropyl and the like.

Alkylene at $R^A$, $R^B$, $R^D$, $R^E$ and $R^9$ may be linear or branched and preferably has 1 to 8 carbon atoms. Examples thereof include methylene, ethylene, trimethylene, propylene, tetramethylene, pentamethylene, hexamethylene, 1,1-dimethylethylene, 2,2-dimethylpropylene and the like.

Alkali metal at A, B, D and E is preferably sodium, potassium and the like.

Halogen atom at X is exemplified by chlorine atom, bromine atom, iodine atom and the like.

When $R^4$ is —NHCO—$R^6$, $R^6$ and $R^5$ may combinedly form a ring. The group (—$R^6$—$R^5$—) formed by $R^6$ and $R^5$ in combination may be linear or branched and preferably has 2 to 12 carbon atoms. Examples thereof include alkylene such as 1,1-dimethyltrimethylene, 1,1-dimethyltetramethylene, 2,2-dimethyltetramethylene, 1,1-dimethylpentamethylene, 2,2-dimethylpentamethylene and the like, and alkylene having —OCO— bond, such as —C(CH$_3$)$_2$CH$_2$OCO(CH$_2$)$_3$—, —C(CH$_3$)$_2$CH$_2$OCOC(CH$_3$)$_2$(CH$_2$)$_3$— and the like.

The preferable Compound (I) of the present invention includes, for example, 1-butyl-3-(1-hexyl-4,6-dimethylindolin-5-yl)urea, 1-butyl-3-(1-hexyl-4,6-dimethylindolin-7-yl)urea, N-(1-hexyl-4,6-dimethylindolin-5-yl)-2,2-dimethylpropanamide, N-(1-hexyl-4,6-dimethylindolin-7-yl)-2,2-dimethylpropanamide, N-(1-pentyl-4,6-dimethylindolin-7-yl)-2,2-dimethylpropanamide, N-(1-isobutyl-4,6-dimethylindolin-7-yl)-2,2-dimethylpropanamide, N-(1-hexyl-4,6-dimethylindolin-7-yl)-2,2-dimethylbutanamide, N-(1-hexyl-4,6-dimethylindolin-7-yl)-2,2-dimethylpentanamide, N-(1-hexyl-4,6-dimethylindolin-7-yl)-cyclohexanamide, N-(1-hexyl-4,6-dimethylindolin-7-yl)-2,2-dimethyl-3-ethoxypropanamide, N-(1-ethoxypropyl-4,6-dimethylindolin-7-yl)-2,2-dimethylpropanamide, N-(1-hexyl-4,6-dimethylindolin-7-yl)-2,2-dimethyl-3-piperidinopropanamide, N-(1-piperidinopropyl-4,6-dimethylindolin-7-yl)-2,2-dimethylpropanamide, N-(1-hexyl-4,6-dimethylindolin-7-yl)-2,6-dimethylpiperidinopropanamide, and the like, and pharmaceutically acceptable salts thereof.

The Compound (I) may be converted to a pharmaceutically acceptable salt thereof.

The Compound (I) may be converted to an acid addition salt, since it has a basic group, and the acid to form this acid addition salt includes, for example, an inorganic acid such as hydrochloric acid, sulfuric acid, phosphoric acid, nitric acid and the like; an organic acid such as oxalic acid, fumaric acid, maleic acid, citric acid, tartaric acid, methanesulfonic acid, toluenesulfonic acid and the like; and the like.

When Compound (I) has an acidic group such as carboxyl, it can form an alkali metal salt such as sodium salt, potassium salt and the like; alkaline earth metal salt such as calcium salt, magnesium salt and the like; organic base salt such as triethylamine salt, dicyclohexylamine salt, pyridine salt and the like; and the like.

The Compound (I) and pharmaceutically acceptable salts thereof can be produced, for example, by the following methods.

Production Method 1

Compound (II) and Compound (III) are Reacted.

This method produces a compound of the formula (I) wherein $R^6$ is —$NR^7R^8$ where $R^8$ is hydrogen atom.

This reaction generally proceeds in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and the like, and mixtures thereof.

In addition, a base such as triethylamine, pyridine, 4-dimethylaminopyridine, potassium carbonate and the like may be added.

The reaction temperature is. generally from −10° C. to 160° C., preferably 20–100° C., and the reaction time is generally from 30 minutes to 10 hours.

The starting compound (II) can be prepared, for example, by the following method.

A nitro group is introduced into a compound of the general formula (x)

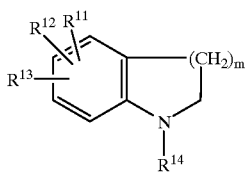
(X)

wherein $R^{11}$, $R^{12}$, $R^{13}$ and m are as defined above and $R^{14}$ is an amino-protecting group (see J. Eric. Mordlander, et al., J. Org. Chem., 46, 778–782 (1981)], (introduction of nitro onto benzene ring) using nitric acid in a mixed solvent of acetic acid and sulfuric acid, and the amino-protecting group is eliminated. The compound thus obtained and compound (IX) are reacted, and nitro group is reduced using a catalyst such as palladium-carbon and the like to give starting compound (II).

Examples of the amino-protecting group at $R^{14}$ include acyl such as formyl, acetyl, monochloroacetyl, dichloroacetyl, trichloroacetyl, trifluoroacetyl, propionyl, benzoyl and the like.

Said amino-protecting group is eliminated by a method known per se. For example, it is eliminated by the action of an acid (e.g., hydrochloric acid, formic acid, trifluoroacetic acid and the like) or an alkali (e.g., sodium hydroxide, potassium hydroxide, sodium carbonate, sodium hydrogencarbonate and the like), or other method.

Production Method 2

Compound (II) and Compound (IV) are Reacted.

This method produces a compound of the formula (I) wherein $R^6$ can be any one of those defined above.

This reaction generally proceeds in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and the like, and mixtures thereof.

In addition, a base such as triethylamine, pyridine, 4-dimethylaminopyridine, potassium carbonate and the like may be added.

The reaction temperature is generally from −10° C. to 100° C., preferably 0–60° C., and the reaction time is generally from 30 minutes to 10 hours.

Production Method 3

Compound (II) and compound (V) or a reactive derivative thereof are reacted.

This method produces a compound of the formula (I) wherein $R^6$ is $R^{6'}$.

This reaction generally proceeds in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and the like, and mixtures thereof.

In addition, a base such as triethylamine, pyridine, 4-dimethylaminopyridine, potassium carbonate and the like may be added.

The reaction temperature is generally from −10° C. to 100° C., preferably 0–60° C., and the reaction time is generally from 30 minutes to 10 hours.

Compound (V) is subjected to said reaction as, for example, a free acid; a salt such as sodium, potassium, calcium, triethylamine, pyridine and the like; or a reactive derivative such as acid anhydride, mixed acid anhydride [e.g., substituted phosphoric acid (e.g., dialkylphosphoric acid), alkyl carbonate (e.g., monoethyl carbonate) and the like], active amide (e.g., amide with imidazole etc.), ester (e.g., cyanomethyl ester, 4-nitrophenyl ester and the like), and the like.

When Compound (V) is used as a free acid or salt in this reaction, the reaction is preferably carried out in the presence of a condensing agent. Examples of the condensing agent include dehydrating agent such as N,N'-di-substituted-carbodiimides (e.g., N,N'-dicyclohexylcarbodiimide), carbodiimide compounds (e.g., 1-ethyl-3-(3'-dimethylaminopropyl)carbodiimide, N-cyclohexyl-N'-morpholinoethylcarbodiimide and N-cyclohexyl-N'-(4-diethylaminocyclohexyl)carbodiimide), azolide compounds (e.g., N,N'-carbonyldiimidazole and N,N'-thionyldiimidazole) and the like. When these condensing agents are used, the reaction is considered to proceed via a reactive derivative of carboxylic acid.

Production Method 4

Compound (VI) and Compound (VII) are Reacted.

This method produces a compound of the formula (I) wherein $R^6$ is —$NR^7R^8$.

This reaction generally proceeds in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and the like, and mixtures thereof.

In addition, a base such as triethylamine, pyridine, 4-dimethylaminopyridine, potassium carbonate and the like may be added.

The reaction temperature is generally from −10° C. to 160° C., preferably 10–100° C., and the reaction time is generally from 30 minutes to 10 hours.

The starting compound (VI) can be produced, for example, by dissolving compound (II) in an inert solvent and bubbling in phosgene.

Production Method 5

Compound (VIII) and Compound (IX) are Reacted.

This reaction generally proceeds in an inert solvent. Examples of the inert solvent include acetone, dioxane, acetonitrile, chloroform, benzene, methylene chloride, ethylene chloride, tetrahydrofuran, ethyl acetate, N,N-dimethylformamide, pyridine, water and the like, and mixtures thereof.

In addition, a base such as triethylamine, pyridine, 4-dimethylaminopyridine, potassium carbonate, sodium hydride and the like may be added.

The reaction temperature is generally from −10° C. to 100° C., preferably 0–60° C., and the reaction time is generally from 30 minutes to 10 hours.

The starting compound (VIII) can be prepared, for example, by the method wherein a nitro group is introduced into a compound of the formula (X) (introduction of nitro onto benzene ring), and the nitro group is reduced using a catalyst such as palladium-carbon and the like to give a compound of the formula (XI)

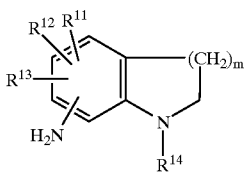

wherein $R^{11}$, $R^{12}$, $R^{14}$ and m are as defined above. Using this compound as a starting compound and according to Production Method 2, a compound of the formula (XII)

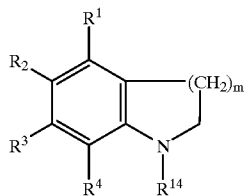

wherein $R^1$, $R^2$, $R^3$, $R^4$, $R^{14}$ and m are as defined above, is obtained. This compound is deprotected to give compound (VIII).

The Compound (I) of the present invention obtained as in the above can be purified by a method conventionally known, such as chromatography and recrystallization.

This Compound (I) can be converted to a pharmaceutically acceptable salt by a method known per se.

The Compound (I) and pharmaceutically acceptable salts thereof of the present invention show superior ACAT inhibitory activity and lipoperoxidation inhibitory activity in mammals (e.g., human, cow, horse, dog, cat, rabbit, rat, mouse, hamster and the like) and are useful as ACAT inhibitors and hyperlipemia inhibitors. To be specific, they are useful for the prevention and treatment of arteriosclerotic lesions such as arteriosclerosis, hyperlipemia and diabetes, as well as ischemic diseases of brain, heart and the like.

A pharmaceutical composition containing Compound (I) or a pharmaceutically acceptable salt thereof of the present invention may contain an additive. Examples of the additive include excipients (e.g., starch, lactose, sugar, calcium carbonate and calcium phosphate), binders (e.g., starch, gum arabic, carboxymethylcellulose, hydroxypropylcellulose and crystalline cellulose), lubricants (e.g., magnesium stearate and talc), disintegrators (e.g., calcium carboxymethylcellulose and talc), and the like.

The above-mentioned ingredients are mixed, and the mixture can be formulated into an oral preparation such as capsule, tablet, fine granules, granules, dry syrup and the like, or a parenteral preparation such as injection, suppository and the like by a method conventionally known.

While the dose of Compound (I) and pharmaceutically acceptable salts thereof of the present invention varies depending on administration target, symptom and other factors, it is generally about 0.1–50 mg/kg body weight per dose for an adult patient with hypercholesterolemia by oral administration in about one to three times a day.

The present invention is described in more detail in the following by way of Examples, to which the present invention is not limited.

EXAMPLE 1

1-Butyl-3-(1-hexyl-4,6-dimethylindolin-5-yl)urea (1) 1-Acetyl-4,6-dimethylindoline 4,6-Dimethylindole (1.08 g) was dissolved in acetic acid (20 ml), and sodium cyanoborohydride (2.3 g) was added portionwise at 15° C. The mixture was stirred at said temperature for one hour and poured into ice water. Saturated aqueous sodium hydrogencarbonate was added to neutralize the mixture and the mixture was extracted with ethyl acetate. The extract was washed with saturated brine and dried over sodium sulfate. The solvent was evaporated under reduced pressure. The residue was dissolved in benzene, and acetic anhydride (840 mg) was added, which was followed by stirring at room temperature for one hour. The reaction mixture was washed with saturated aqueous sodium hydrogencarbonate and saturated brine, and dried over sodium sulfate. The solvent was evaporated under reduced pressure. The residue was purified by silica gel column chromatography (developing solvent: chloroform-methanol=1:0–10:1) to give 1.3 g of the title compound (1).

$^1$H—NMR (CDCl$_3$) δ: 2.18 (6H, s, —CH$_3$, —COCH$_3$), 2.30 (3H, s, —CH$_3$), 3.00 (2H, t, J=8.3 Hz, C$_3$—H$_2$), 4.03 (2H, t, J=8.3 Hz, C$_2$—H$_2$), 6.66 (1H, s, C$_5$—H), 7.89 (1H, s, C$_7$—H).

(2) 1-Acetyl-4,6-dimethyl-5-nitroindoline

1-Acetyl-4,6-dimethylindoline (2.6 g) was dissolved in acetic anhydride (35 ml), and nitric acid (d=1.5, 0.92 ml) dissolved in acetic anhydride (15 ml) was added dropwise at 0° C. The mixture was stirred at room temperature for one hour and poured into ice water. Saturated aqueous sodium hydrogencarbonate was added to neutralize the mixture, and the mixture was extracted with chloroform. The extract was washed with saturated brine and dried over sodium sulfate. The solvent was evaporated under reduced pressure. The residue was purified by silica gel column chromatography (developing solvent: chloroform-methanol=1:0–100:1) to give 2.4 g of the title compound (2).

$^1$H—NMR (CDCl$_3$) δ: 2.17 (3H, s, —COCH$_3$), 2.24 (3H, s, —CH$_3$), 2.30 (3H, s, —CH$_3$), 3.08 (2H, t, J=8.4 Hz, C$_3$—H$_2$), 4.14 (2H, t, J=8.3 Hz, C$_2$—H$_2$), 8.00 (1H, s, C$_7$—H).

(3) 4,6-Dimethyl-1-hexyl-5-nitroindoline

1-Acetyl-4,6-dimethyl-5-nitroindoline (2.4 g) obtained in (2) was dissolved in methanol. (25 ml) and 6N hydrochloric acid (20 ml) was added, which was followed by refluxing for 15 hours. After the completion of the reaction, the solvent was evaporated under reduced pressure. The residue was dissolved in chloroform, and the mixture was washed with saturated aqueous sodium hydrogencarbonate and saturated brine, and dried over sodium sulfate. The solvent was evaporated under reduced pressure. Indoline (1.8 g) thus obtained was dissolved in dimethylformamide (20 ml), and sodium hydride (abt. 60% in oil suspension, 457 mg) was added at 0° C. The mixture was stirred at said temperature for 0.5 hour and hexyl bromide (1.8 g) was added to the reaction mixture, which was followed by stirring at room temperature for 3 hours. Water was added to the reaction mixture, and the mixture was extracted with ethyl acetate. The extract was washed with saturated brine and dried over sodium sulfate. The solvent was evaporated under reduced pressure. The residue was purified by silica gel column chromatography (developing solvent:hexane-ethyl acetate=1:0–10:1) to give 2.8 g of the title compound (3).

$^1$H—NMR (CDCl$_3$) δ: 0.90 (3H, br-t, —CH$_3$), 1.2–1.8 (8H, m, —(CH$_2$)$_4$—), 2.17 (3H, s, —CH$_3$), 2.30 (3H, s, —CH$_3$), 3.00 (2H, t, J=8.4 Hz, C$_3$—H$_2$), 3.09 (2H, t, J=7.2 Hz, N—CH$_2$), 3.51 (2H, t, J=8.3 Hz, C$_2$—H$_2$), 5.99 (1H, s, C$_7$—H).

(4) 1-Butyl-3-(1-hexyl-4,6-dimethylindolin-5-yl)urea 4,6-Dimethyl-1-hexyl-5-nitroindoline (1.0 g) obtained in (3) was dissolved in benzene (40 ml) and 10% palladium-carbon (100 mg) was added to allow hydrogenation at 40° C. After the completion of the reaction, palladium-carbon was filtered off, and the filtrate was washed with saturated aqueous sodium hydrogencarbonate and saturated brine, and dried over sodium sulfate. The solvent was evaporated under reduced pressure. 5-Amino-4,6-dimethyl-1-hexylindoline thus obtained was dissolved in chloroform (20 ml) and butyl isocyanate (400 mg) was added to the reaction mixture, which was followed by stirring at room temperature for 18 hours. Water was added to the reaction mixture, and the mixture was washed with saturated brine and dried over sodium sulfate. The solvent was evaporated under reduced pressure. The residue was purified by silica gel column chromatography (developing solvent:chloroform-methanol= 1:0–50:1) and recrystallized from ethanol to give 650 mg of the title compound (4).

$^1$H—NMR (CDCl$_3$) δ: 0.91 (6H, br-t, —CH$_3$), 1.0–2.0 (12H, m, —(CH$_2$)$_4$—, —(CH$_2$)$_2$—), 2.09 (3H, s, —CH$_3$), 2.19 (3H, s, —CH$_3$), 2.6–3.6 (8H, m, NH—CH$_2$, C$_3$—H$_2$, N—CH$_2$, C$_2$—H$_2$), 4.29 (1H, br, NH), 5.45 (1H, br, NH), 6.18 (1H, S, C$_7$—H).

EXAMPLE 2

N-(1-Hexyl-4,6-dimethylindolin-5-yl)-2,2-dimethylpropanamide

5-Amino-4,6-dimethyl-1-hexylindoline (880 mg) was dissolved in chloroform (20 ml), and triethylamine (370 mg) and pivaloyl chloride (430 mg) were added, which was followed by stirring at room temperature for 1 hour. Water was added to the reaction mixture, and the mixture was washed with saturated brine and dried over sodium sulfate. The solvent was evaporated under reduced pressure. The residue was purified by silica gel column chromatography (developing solvent:chloroform-methanol=1:0–50:1) and recrystallized from ethanol to give 650 mg of the title compound.

$^1$H—NMR (CDCl$_3$) δ: 0.84 (3H, br-t, —CH$_3$), 1.1–1.8 (8H, m,—(CH$_2$)$_4$—) 1.33 (9H, s, —(CH$_3$)$_3$), 2.00 (3H, s, —CH$_3$), 2.11 (3H, s, —CH$_3$), 2.82 (2H, t, J=7.8 Hz, C$_3$—H$_2$), 2.99 (2H, t, J=7.2 Hz, N—CH$_2$), 3.33 (2H, t, J=7.8 Hz, C$_2$—H$_2$), 6.16 (1H, s, C$_7$—H), 6.70 (1H, br, N—H).

EXAMPLE 3

N-(1-Hexyl-4,6-dimethylindolin-7-yl)-2,2-dimethylpropanamide (1) 1-Acetyl-5-bromo-4,6-dimethylindoline 1-Acetyl-4,6-dimethylindoline (5.5 g) was dissolved in acetic acid (150 ml), and bromine (2.2 ml) was added dropwise at room temperature. The mixture was stirred at room temperature for 1 hour, and poured into ice water. The precipitated solid was collected by filtration, and recrystallized from methanol to give 6.5 g of the title compound (1).

$^1$H—NMR (CDCl$_3$) δ: 2.19 (3H, s,—COCH$_3$), 2.27 (3H, s, —CH$_3$), 2.39 (3H, s, —CH$_3$), 3.06 (2H, t, J=8.4 Hz, C$_3$—H$_2$), 4.03 (2H, t, J=8.4 Hz, C$_2$—H$_2$), 7.99 (1H, s, C$_7$—H).

(2) 5-Bromo-4,6-dimethyl-7-nitroindoline

Concentrated sulfuric acid (25 ml) and nitric acid (d=1.56, 1.46 ml) were added to acetic acid (25 ml), and 1-acetyl 5-bromo-4,6-dimethylindoline (6.5 g) obtained in (1) was added while stirring the mixture at 0° C., which was followed by stirring at said temperature for 18 hours. The reaction mixture was poured into ice water, and the precipitated solid was collected by filtration and washed thoroughly with water. The obtained solid was suspended in ethanol (50 ml) and water (10 ml). Sodium hydroxide (20 g) was added and the mixture was refluxed for 3 hours. The solvent was evaporated under reduced pressure and chloroform was added. The mixture was washed with saturated brine and dried over sodium sulfate. The solvent was evaporated under reduced pressure. The residue was purified by silica gel column chromatography (developing solvent:benzene) to give 4.8 g of the title compound (2).

$^1$H—NMR (CDCl$_3$) δ: 2.29 (3H, s, C$_4$—CH$_3$), 2.65 (3H, s, C$_6$—CH$_3$), 3.10 (2H, t, J=8.4 Hz, C$_3$—H$_2$), 3.82 (2H, t, J=8.4 Hz, C$_2$—H$_2$), 9.0 (1H, br, N—H).

(3) N-(1-Hexyl-4,6-dimethylindolin-7-yl)-2,2-dimethylpropanamide

5-Bromo-4,6-dimethyl-7-nitroindoline (3.0 g) obtained in (2) was dissolved in dimethylformamide (60 ml) and sodium hydride (abt. 60% in oil suspension, 530 mg) was added at 0° C., which was followed by stirring at said temperature for 0.5 hour. Hexyl bromide (1.8 g) was added to the reaction mixture and the mixture was stirred at room temperature for 12 hours. Water was added to the reaction mixture, and the mixture was extracted with ethyl acetate. The extract was washed with saturated brine and dried over sodium sulfate. The solvent was evaporated under reduced pressure. The residue was purified by silica gel column chromatography (developing solvent:hexane-ethyl acetate=1:0–10:1). The obtained solid was dissolved in benzene (40 ml) and 10% palladium-carbon (100 mg) was added to allow hydrogenation at 40° C. After the completion of the reaction, palladium-carbon was filtered off, and the filtrate was washed with saturated aqueous sodium hydrogencarbonate and saturated brine, and dried over sodium sulfate. The solvent was evaporated under reduced pressure.

7-Amino-4,6-dimethyl-1-hexylindoline thus obtained was dissolved in chloroform (20 ml), and triethylamine (1.0 g) and pivaloyl chloride (1.0 g) were added to the reaction mixture, which was followed by stirring at room temperature for 1 hour. Water was added to the reaction mixture, and the mixture was washed with saturated brine and dried over sodium sulfate. The solvent was evaporated under reduced pressure. The residue was purified by silica gel column chromatography (developing solvent:chloroform-methanol= 1:0–50:1). The obtained compound (3) was dissolved in ethanol and 10 N hydrochloric acid/ethanol (1 ml) was added. The solvent was evaporated under reduced pressure. The residue was recrystallized from ethanol to give 700 mg of hydrochloride of the title compound (3).

$^1$H—NMR (CDCl$_3$) δ: 0.90 (3H, br-t, —CH$_3$), 1.1–1.6 (8H, m, —(CH$_2$)$_4$—), 1.41 (9H, s, —(CH$_3$)$_3$), 2.15 (3H, s, —CH$_3$), 2.25 (3H, s, —CH$_3$), 3.15 (4H, m, C$_3$—H$_2$, N—CH$_2$), 3.70 (1H, m, C$_2$—H), 4.00 (1H, m, C$_2$—H), 7.12 (1H, s, C$_5$—H), 9.2 (1H, br, N—H).

EXAMPLE 4

1-Butyl-3-(1-hexyl-4,6-dimethylindolin-7-yl)urea

7-Amino-4,6-dimethyl-1-hexylindoline (800 mg) was dissolved in chloroform (20 ml) and butyl isocyanate (400 mg) was added, which was followed by stirring at room temperature for 18 hours. Water was added to the reaction mixture, and the mixture was washed with saturated brine and dried over sodium sulfate. The solvent was evaporated under reduced pressure. The residue was purified by silica gel column chromatography (developing solvent:chloroform-methanol=1:0–50:1) and recrystallized from ethanol to give 450 mg of the title compound.

¹H—NMR (CDCl₃) δ: 0.88 (6H, br-t, —CH₃), 1.0–1.8 (12H, m, —(CH₂)₄—, —(CH₂)2—), 2.13 (6H, s, —CH₃×2), 2.83 (2H, t, J=8.3 Hz, C₃—H₂), 3.20(4H, N—CH₂×2), 3.43 (2H, t, J=8.3 Hz, C₂—H₂), 4.80 (1H, br-t, NH—CH₂), 5.52 (1H, br-s, C₇—NH), 6.40 (1H, s, C₅—H).

EXAMPLES 5–36

In the same manner as in any one of the above-mentioned Examples 1–4, the compounds shown in Tables 1 and 2 were obtained.

TABLE 1

[Structure: indoline with R¹ at 4-position, R² at 5, R³ at 6, R⁴ at 7, R⁵ on N]

R⁴ = —NHCO—R⁶

| Example | R¹ | R² | R³ | R⁶ | R⁵ |
|---|---|---|---|---|---|
| 5 | —H | —H | —CH₃ | —C(CH₃)₃ | —(CH₂)₅CH₃ |
| 6 | —CH₃ | —H | —CH₃ | —C(CH₃)₂(CH₂)₈CH₃ | —CH₂CH₂ |
| 7 | —OCH₃ | —H | —OCH₃ | —C(CH₃)₃ | —(CH₂)₅CH₃ |
| 8 | —CH₃ | —H | —CH₃ | —C(CH₃)₃ | —(CH₂)₃CH₃ |
| 9 | —CH₃ | —H | —CH₃ | —C(CH₃)₂(CH₂)₃CH₃ | —(CH₂)₃CH₃ |
| 10 | —CH₃ | —H | —CH₃ | —C(CH₃)₂(CH₂)₅CH₃ | —(CH₂)₃CH₃ |
| 11 | —CH₃ | —H | —CH₃ | —C(CH₃)₃ | —(CH₂)₇CH₃ |
| 12 | —CH₃ | —H | —CH₃ | —C(CH₃)₃ | —CH₂CH₃ |
| 13 | —CH₃ | —H | —CH₃ | —C(CH₃)₂(CH₂)₅CH₃ | —CH₂CH₃ |
| 14 | —CH₃ | —H | —CH₃ | —C(CH₃)₂(CH₂)₃CH₃ | —(CH₂)₅CH₃ |
| 15 | —CH₃ | —H | —CH₂ | —C(CH₃)₂(CH₂)₅CH₃ | —(CH₂)₅CH₃ |
| 16 | —CH₃ | —H | —CH₃ | —CH₃ | —(CH₂)₅CH₃ |
| 17 | —CH₃ | —H | —CH₃ | —CH(CH₃)₂ | —(CH₂)₅CH₃ |
| 18 | —CH₃ | —H | —CH₃ | —CH₂C(CH₃)₂CH₂COOH | —(CH₂)₅CH₃ |
| 19 | —CH₂CH₃ | —H | —CH₂CH₃ | —C(CH₃)₃ | —(CH₂)₅CH₃ |
| 20 | —CH₃ | —H | —CH₃ | —C(CH₃)₂(CH₂)₂COOH | —(CH₂)₅CH₃ |

TABLE 2

[Structure: indoline with R¹, R², R³, R⁴, R⁵]

R⁴ = —NHCO—R⁶

| Example | R¹ | R² | R³ | R⁶ | R⁵ |
|---|---|---|---|---|---|
| 21 | —CH₃ | —H | —CH₃ | —(CH₂)₃CH₃ | —(CH₂)₅CH₃ |
| 22 | —CH₃ | —H | —CH₃ | —C(CH₃)₃ | —(CH₂)₂OCOCH₃ |
| 23 | —CH₃ | —H | —CH₃ | —C(CH₃)₃ | —(CH₂)₂OCH₃ |
| 24 | —CH₃ | —H | —CH₃ | —C(CH₃)₃ | —(CH₂)₂OC₂H₅ |
| 25 | —CH₃ | —H | —CH₃ | —C(CH₃)₃ | —C₅H₁₁ |
| 26 | —CH₃ | —H | —CH₃ | —C(CH₃)₃ | —(CH₂)₅COOH |
| 27 | —CH₃ | —H | —CH₃ | —C(CH₃)₃ | —C₇H₁₅ |
| 28 | —CH₃ | —H | —CH₃ | —C(CH₃)₂CH₂OH | —C₆H₁₃ |
| 29 | —CH₃ | —H | —CH₃ | —C(CH₃)₂CH₂OCOCH₃ | —C₈H₁₃ |
| 30 | —CH₃ | —H | —CH₃ | [3-pyridyl] | —C₈H₁₃ |
| 31 | —CH₃ | —H | —CH₃ | —C(CH₃)₃ | —(CH₂)₂CH(CH₃)₂ |
| 32 | —CH₃ | —H | —CH₃ | C(CH₃)₃ | —CH₂CH(CH₃)₂ |

TABLE 2-continued

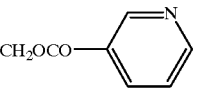

R⁴ = —NHCO—R⁶

| Example | R¹ | R² | R³ | R⁶ | R⁵ |
|---|---|---|---|---|---|
| 33 | —CH₃ | —H | —CH₃ | —C(CH₃)₂CH₂OCO-(3-pyridyl) | —C₈H₁₃ |
| 34 | —CH₃ | —H | —CH₃ | —C(CH₃)₂CH₂OC₂H₅ | —C₈H₁₃ |
| 35 | —CH₃ | —H | —CH₃ | —CH₂CH₂—N(2,6-dimethylpiperidinyl) | —C₈H₁₃ |
| 36 | —CH₃ | —H | —CH₃ | —C(CH₃)₃ | —C₃H₇ |

The ¹H—NMR data of the compounds of the above Examples 5–36 are shown in the following.

¹H—NMR (CDCl₃) δ:

Example 5:(hydrochloride). 0.91 (3H, br-t), 1.1–1.8 (8H, m), 1.34 (9H, s), 2.09 (3H, s), 2.93–3.48 (4H, m), 3.48–3.82 (1H, m), 3.82–4.35(1H, m), 7.12 (1H, d), 7.32 (1H, d), 9.36 (1H, br-s).

Example 6:0.93 (3H, br-t), 1.0–2.0 (19H, m), 1.35 (6H, s), 2.12 (3H, s), 2.19 (3H, s), 2.98 (2H, t), 3.25 (2H, t), 3.65 (2H, t), 6.80 (1H, s), 8.09 (1H, br-s).

Example 7:0.87 (3H, br-t), 1.1–1.8 (8H, m), 1.31 (9H, s), 2.84 (2H, t), 3.16 (2H, t), 3.44 (2H, t), 3.74 (3H, s), 3.79 (3H, s), 5.86 (1H, s).

Example 8:0.92 (3H, br-t), 1.39 (9H, s), 1.2–1.9 (4H, m), 2.08 (3H, s), 2.15 (3H, s), 2.80–3.30 (4H, m), 3.60 (2H, t), 6.68(1H, s), 7.78 (1H, br-s).

Example 9:0.90 (3H, br-t), 0.92 (3H, br-t), 1.08–1.88 (10H, m), 1.29 (6H, s), 2.05 (3H, s), 2.12 (3H, s), 2.81 (2H, t), 3.13 (2H, t), 3.40 (2H, t), 6.39 (1H, s), 6.74 (1H, br-s).

Example 10:0.63–1.05 (6H, m), 1.05–1.82 (14H, m), 1.29 (6H, s), 2.08(3H, s), 2.10 (3H, s), 2.82 (2H, s), 3.13 (2H, t), 3.41 (2H,t), 6.41 (1H,.s), 6.77 (1H, br-s).

Example 11:0.88 (3H, br-t), 1.01–1.87 (12H, m), 1.35 (9H, s), 2.09 (3H, s), 2.14 (3H, s), 2.82 (2H, t), 3.13 (2H, t), 3.52 (2H, t), 6.60 (1H, br-s).

Example 12:1.18 (3H, t), 1.35 (9H, s), 2.09 (3H, s), 2.15 (3H, s), 2.92 (2H, t), 3.22 (2H, q), 3.56 (2H, t), 6.62 (1H, s), 7.57 (1H, br-s).

Example 13:0.88 (3H, br-t), 1.08 (3H, t), 1.29 (6H, s), 1.1–1.9 (10H, m), 2.08 (3H, s), 2.22 (3H, s), 2.82 (2H, t), 3.21 (2H, q), 3.33 (2H, t), 6.43 (1H, s), 6.84 (1H, br-s).

Example 14:0.90 (3H, br-t), 0.92 (3H, br-t), 1.08–1.88 (14H, m), 1.29 (6H, s), 2.05 (3H, s), 2.12 (3H, s), 2.81 (2H, t), 3.13 (2H, t), 3.40 (2H, t), 6.39 (1H, s), 6.74 (1H, br-s).

Example 15:0.63–1.05 (6H, m), 1.05–1.82 (18H, m), 1.34 (6H, s), 2.11 (31H, s), 2.17 (3H, s), 2.95 (2H, s), 3.13 (2H, t), 3.60 (2H, t), 6.72 (1H, s), 7.8 (1H, br).

Example 16:0.89 (3H, br-t), 1.05–1.70 (8H, m), 1.81 (3H₁, s), 2.11 (3H, s), 2.15 (3H, s), 2.81 (2H, br-t), 2.6–3.8 (4H, m), 6.39 (1H, s), 6.58 (4H, br), 6.72 (1H, br).

Example 17:0.87 (3H, br-t), 1.05–1.90 (8H, m), 1.25 (3H, s), 1.32 (3H, s), 2.11 (3H, s), 2.17 (3H, s), 2.67 (1H, m), 2.7–3.4 (4H, m), 3.59 (2H, t), 6.69 (1H, s), 7.83 (1H, br-s).

Example 18:0.87 (3H, br-t), 1.05–1.80 (8H, m), 1.21 (6H, s), 2.17 (6H, s), 2.48 (2H, s), 2.55 (2H, s), 3.01 (2H, t), 3.10 (2H, t), 3.54 (2H, t), 6.70 (1H, s), 6.8–8.2 (1H, br-s), 8.72 (1H, br-s).

Example 19:0.87 (3H, br-t), 1.05–1.80 (8H, m), 1.17 (3H, t), 1.20 (3H, t), 1.35 (9H, s), 2.22–2.62 (4H, m), 2.91 (2H, t), 3.04 (2H, t), 3.48 (2H, br-t), 6.56 (1H, s), 7.25 (1H, br-s).

Example 20:0.85 (3H, br-t), 1.05–1.80 (8H, m), 1.27 (6H, s), 1.80–2.25 (2H, m), 2.10 (3H, s), 2.16 (3H, s), 2.25–2.55 (2H, m), 2.90 (2H, t), 3.04 (2H, t), 3.47 (2H, t), 6.69 (1H, s), 8.49 (1H, br-s), 8.95 (1H, br-s).

Example 21:0.83 (3H, br-t), 0.87 (3H, br-t), 1.1–1.8 (11H, m), 2.11 (3H, s), 2.16 (3H, s) 2.29 (1H, t), 2.85 (2H, t), 3.22 (2H, t), 3.55 (2H, t), 6.49 (1H, s), 6.68 (1H, br).

Example 22:1.27 (9H, s), 2.04 (6H, s), 2.13 (3H, s), 3.06 (2H, t), 3.43 (2H, t), 3.75 (2H, t), 4.29 (2H, t), 6.87 (1H, s), 9.15 (1H, br-s).

Example 23:1.33 (9H, s), 2.04 (3H, s), 2.09 (3H, s), 2.8–2.9 (4H, m), 3.38 (3H, s), 3.4–3.6 (4H, m), 6.36 (1H, s), 7.35 (1H, br-s).

Example 24:1.16 (3H, t), 1.32 (9H, s), 2.04 (3H, s), 2.09 (3H,s), 2.82 (2H, t), 3.3–3.6 (8H, m), 6.53 (1H, s), 7.40 (1H, br-s).

Example 25:0.88 (3H, br-t), 1.35 (9H, s), 1.2–1.9 (6H, m), 2.08(3H, s), 2.15 (3H, s), 2.92 (2H, t), 3.13 (2H t), 3.55 (2H, t), 6.23 (1H, s), 7.60 (1H, br-s).

Example 26:1.1–1.9 (6H, m), 1.39 (9H, s), 2.07 (3H, s), 2.13 (3H, s), 2.29 (2H, t), 2.84 (2H, t), 3.11 (2H, t), 3.43 (2H, t), 5.40 (1H, br), 6.52 (1H, s), 7.30 (1H, br-s).

Example 27:0.87 (3H, br-t), 1.1–1.8 (10H, m), 1.34 (9H, s), 2.07 (3H, s), 2.13 (3H, s), 2.87 (2H, t), 3.13 (2H, t), 3.49 (2H, t), 6.52 (1H, s), 7.20 (1H, br-s).

Example 28:0.87 (3H, br-t), 1.1–1.8 (8H, m), 1.26 (6H, s), 1.99 (3H, s), 2.08 (3H, s), 2.78 (2H, t), 3.10 (2H, t), 3.37 (2H, t), 3.48 (2H, s), 4.00 (1H, br-s), 6.35 (1H, s), 7.81 (1H, s).

Example 29:0.87 (3H, br-t), 1.1–1.8 (8H, m), 1.28 (6H, s), 2.07 (6H, s), 2.12 (3H, s), 2.84 (2H, t), 3.14 (2H, t), 3.43 (2H, t), 4.20 (2H, s), 6.48 (1H, s), 7.35 (1H, s).

Example 30:0.87 (3H, br-t), 1.1–8 (8H, m), 2.15 (6H, s), 2.82 (2H, t), 3.16 (2H, t), 3.43 (2H, t), 6.43 (1H, s), 7.42 (2H, m), 8.22 (1H, m), 8.75 (1H, m), 9.16 (1H, br-s).

Example 31:0.90 (6H, d), 1.3–1.8 (3H,m), 1.36 (9H, s), 2.09 (3H, s), 2.16 (3H, s), 2.92 (2H, t), 3.16 (2H, t), 3.54 (2H, t), 6.65 (1H, s), 7.65 (1H, br-s).

Example 32:0.94 (6H, d), 1.33 (9H, s), 1.7–2.0 (1H, m), 2.04 (3H, s), 2.10 (3H, s), 2.82 (2H, t), 2.94 (2H, t), 3.38 (2H, t), 6.37 (1H, s), 6.70 (1H, br-s).

Example 33:0.85 (3H, br-t), 1.1–1.8 (8H, m), 1.44 (6H, s), 2.03 (3H, s), 2.08 (3H, s), 2.80 (2H, t), 3.14 (2H, t), 3.41 (2H, t), 4.50 (2H, s), 6.37 (1H, s), 7.04 (1H, br-s), 7.40 (2H, m), 8.28 (1H, m), 8.75 (1l, m), 9.21 (1H, d).

Example 34:0.88 (3H, br-t), 1.1–1.8 (8H, m), 1.23 (3H, t), 1.27 (6H, s), 2.07 (3H, s), 2.10 (3H, s), 2.81 (2H, t), 3.18 (2H, t), 3.41 (2H, t), 3.48 (2H, s), 3.55 (2H, q), 6.37 (1H, s), 8.00 (1H, br-s).

Example 35:0.88 (3H, br-t), 1.1–1.8 (14H, m), 1.24 (6H, s), 2.10 (6H, s), 2.50 (2H, t), 2.90 (2H, t), 2.8–3.6 (8H, m), 6.39 (1H, s), 7.00 (1H, br-s).

Example 36:0.87 (3H, br-t), 1.2–1.9 (2H, m), 1.35 (9H, s), 2.08 (3H, s), 2.15 (3H, s), 2.93 (2H, t), 3.12 (2H, t), 3.50 (2H, t), 6.30 (1H, s), 7.40 (1H, br-s).

In the same manner as in any one of the above-mentioned Examples 1–4, the compounds shown in Tables 3 to 9 can be obtained.

TABLE 3

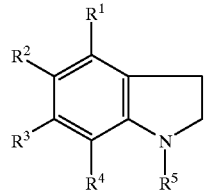

$R^4 = $ —NHCO—$R^6$

| Example | $R^1$ | $R^2$ | $R^3$ | $R^6$ | $R^5$ |
|---|---|---|---|---|---|
| 37 | —$CH_3$ | —H | —$CH_3$ | —$C(CH_3)_3$ | —$CH_2$—CH=$C(CH_3)_2$ |
| 38 | —$CH_3$ | —H | —$CH_3$ | —$C(CH_3)_3$ | —$(CH_2)_4SO_3Na$ |
| 39 | —$CH_3$ | —H | —$CH_3$ | —$C(CH_3)_3$ | —$(CH_2)_3$—N(piperidine) |
| 40 | —$CH_3$ | —H | —$CH_3$ | —$C(CH_3)_3$ | —$(CH_2)_4$—N(piperidine) |
| 41 | —$CH_3$ | —H | —$CH_3$ | —$C(CH_3)_3$ | —$(CH_2)_3$—N(piperazine)—$CH_3$ |
| 42 | —$CH_3$ | —H | —$CH_3$ | cyclohexyl | —$CH_2CH_3$ |
| 43 | —$CH_3$ | —H | —$CH_3$ | cyclohexyl | —$(CH_2)_2CH_3$ |
| 44 | —$CH_3$ | —H | —$CH_3$ | 4-(aminomethyl)cyclohexyl | —$(CH_2)_5CH_3$ |

TABLE 3-continued
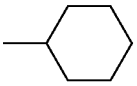
R⁴ = —NHCO—R⁶
| Example | R¹ | R² | R³ | R⁶ | R⁵ |
|---|---|---|---|---|---|
| 45 | —CH₃ | —H | —CH₃ | 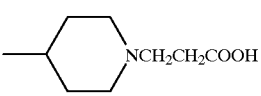 | —(CH₂)₅COOH |
| 46 | —CH₃ | —H | —CH₃ | 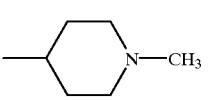 | —(CH₂)₅CH₃ |
| 47 | —CH₃ | —H | —CH₃ | 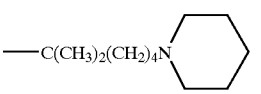 | —(CH₂)₅CH₃ |
| 48 | —CH₃ | —H | —CH₃ | —C(CH₃)₂(CH₂)₄N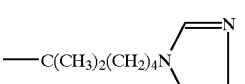 | —(CH₂)₅CH₃ |
| 49 | —CH₃ | —H | —CH₃ | —C(CH₃)₂(CH₂)₄N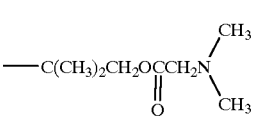 | —(CH₂)₅CH₃ |
| 50 | —CH₃ | —H | —CH₃ | —C(CH₃)₂CH₂OCCH₂N(CH₃)(CH₃)  (with C=O) | —(CH₂)₅CH₃ |
| 51 | —CH₃ | —H | —CH₃ | —C(CH₃)₂—(CH₂)₂—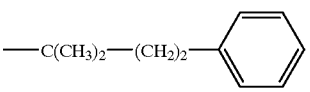 | —CH₂CH₃ |
| 52 | —CH₃ | —H | —CH₃ | —(CH₂)₄OC(CH₃)₃ | —(CH₂)₃CH₃ |
| 53 | —CH₃ | —H | —CH₃ | —C(CH₃)₂—(CH₂)₂O—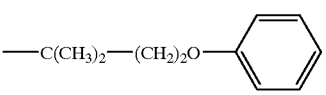 | —(CH₂)₃CH₃ |

TABLE 4

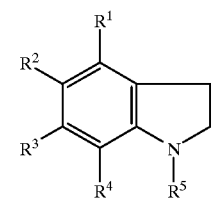

R⁴ = —NHCO—R⁶

| Example | R¹ | R² | R³ | R⁶ | R⁵ |
|---|---|---|---|---|---|
| 54 | —CH₃ | —H | —CH₃ | 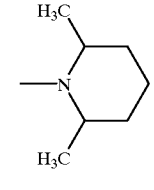 —C(CH₃)₂—(CH₂)₆—N(CH₃)(CH₂C₆H₅) | —CH₂CH₃ |
| 55 | —CH₃ | —H | —CH₃ | —C(CH₃)₂—(CH₂)₆—N(piperidine) | —CH₂CH₃ |
| 56 | —CH₃ | —H | —CH₃ | —C(CH₃)₂—(CH₂)₆—N(4-benzylpiperazine) | —CH₂CH₃ |
| 57 | —CH₃ | —H | —CH₃ | —CH₂C(CH₃)₃ | —(CH₂)₅CH₃ |
| 58 | —CH₃ | —H | —CH₃ | —C(CH₃)₂(CH₂)₂SO₃Na | —(CH₂)₅CH₃ |
| 59 | —CH₃ | —H | —CH₃ | —CH₂C(CH₃)₂(CH₂)₂SO₃Na | —(CH₂)₅CH₃ |
| 60 | —CH₃ | —H | —CH₃ | 2,6-dimethyl-1-piperidinyl | —(CH₂)₅CH₃ |
| 61 | —CH₃ | —H | —CH₃ | 2,4,5-trimethyl-4-methylpiperazinyl 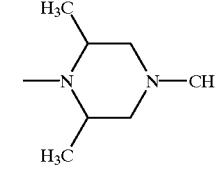 | —(CH₂)₅CH₃ |
| 62 | —H | —H | —OCH₃ | —C(CH₃)₃ | —(CH₂)₆CH₃ |
| 63 | —H | —H | —OCH₃ | —C(CH₃)₃ | —(CH₂)₄CH₃ |
| 64 | —H | —H | —OCH(CH₃)₂ | —C(CH₃)₃ | —(CH₂)₅CH₃ |
| 65 | —H | —H | —OCH(CH₃)₂ | —C(CH₃)₃ | —(CH₂)₄CH₂ |
| 66 | —H | —H | —OCH(CH₃)₂ | —(CH₂)₃CH₃ | —(CH₂)₅CH₃ |
| 67 | —H | —H | —OCH(CH₃)₂ | —(CH₂)₅CH₃ | —(CH₂)₅CH₃ |

TABLE 5

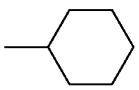

R⁴ = —NHCO—R⁶

| Example | R¹ | R² | R³ | —R⁶—R⁵— |
|---------|-----|-----|-----|---------|
| 68 | —CH₃ | —H | —CH₃ | —C(CH₃)₂(CH₂)₂— |
| 69 | —CH₃ | —H | —CH₃ | —CH₂C(CH₃)₂(CH₂)₂— |
| 70 | —CH₃ | —H | —CH₃ | —C(CH₃)₂CH₂OCO(CH₂)₃— |
| 71 | —CH₃ | —H | —CH₃ | —C(CH₃)₂CH₂OCOC(CH₃)₂(CH₂)₃— |

TABLE 6

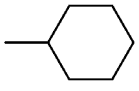

R⁴ = —NHCONH—R⁷

| Example | R¹ | R² | R³ | R⁷ | R⁵ |
|---------|-----|-----|-----|-----|-----|
| 72 | —H | —H | —CH₃ | —C(CH₃)₃ | —(CH₂)₅CH₃ |
| 73 | —CH₃ | —H | —CH₃ | 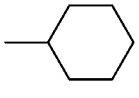 | —(CH₂)₅CH₃ |
| 74 | —OCH₃ | —H | —OCH₃ | —C(CH₃)₃ | —(CH₂)₅CH₃ |
| 75 | —CH₃ | —H | —CH₃ | —C(CH₃)₃ | —(CH₂)₃CH₃ |
| 76 | —CH₃ | —H | —CH₃ |  | —(CH₂)₃CH₃ |
| 77 | —CH₃ | —H | —CH₃ | —C(CH₂)₃ | —(CH₂)₇CH₃ |
| 78 | —CH₃ | —H | —CH₃ | —C(CH₃)₃ | —CH₂CH₃ |
| 79 | —CH₃ | —H | —CH₃ |  | —CH₂CH₃ |
| 80 | —CH₃ | —H | —CH₃ | —(CH₂)₅CH₃ | —(CH₂)₅CH₃ |
| 81 | —H | —H | —CH₃ | —CH₃ | —(CH₂)₅CH₃ |
| 82 | —H | —R | —CH₃ | —(CH₂)₃CH₃ | —(CH₂)₅CH₃ |
| 83 | —H | —H | —CH₃ | —(CH₂)₅CH₃ | —(CH₂)₅CH₃ |
| 84 | —H | —H | —CH₃ | —CH₃ | —(CH₂)₇CH₃ |
| 85 | —H | —H | —CH₃ | —(CH₂)₃CH₃ | —(CH₂)₇CH₃ |
| 86 | —H | —H | —CH₃ | —(CH₂)₅CH₃ | —(CH₂)₇CH₃ |
| 87 | —H | —H | —OCH₃ | —CH₂ | —CH₂CH₃ |
| 88 | —H | —H | —OCH₃ | —(CH₂)₃CH₃ | —CH₂CH₃ |
| 89 | —H | —H | —OCH₃ | —(CH₂)₅CH₃ | —CH₂CH₃ |
| 90 | —H | —H | —OCH₃ | —CH₃ | —(CH₂)(₃CH₃ |

TABLE 6-continued

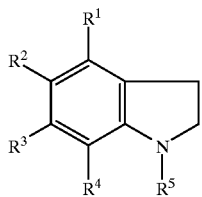

$R^4 = $ —NHCONH—$R^7$

| Example | $R^1$ | $R^2$ | $R^3$ | $R^7$ | $R^5$ |
|---|---|---|---|---|---|
| 91 | —H | —H | —OCH$_3$ | —(CH$_2$)$_3$CH$_3$ | —(CH$_2$)$_3$CH$_3$ |
| 92 | —H | —H | —OCH$_2$ | —(CH$_2$)$_5$CH$_3$ | —(CH$_2$)$_3$CH$_3$ |

TABLE 7

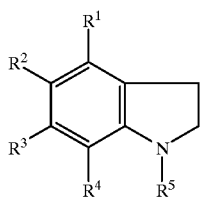

$R^2 = $ —NHCONH—$R^7$

| Example | $R^1$ | $R^3$ | $R^4$ | $R^7$ | $R^5$ |
|---|---|---|---|---|---|
| 93  | —H    | —CH$_3$  | —H | —C(CH$_3$)$_3$             | —(CH$_2$)$_5$CH$_3$ |
| 94  | —CH$_3$  | —CH$_3$  | —H | —C(CH$_3$)$_2$(CH$_2$)$_8$CH$_3$ | —(CH$_2$)$_5$CH$_3$ |
| 95  | —OCH$_3$ | —OCH$_3$ | —H | —C(CH$_3$)$_3$             | —(CH$_2$)$_5$CH$_3$ |
| 96  | —CH$_3$  | —CH$_3$  | —H | —C(CH$_3$)$_3$             | —(CH$_2$)$_3$CH$_3$ |
| 97  | —CH$_3$  | —CH$_3$  | —H | —C(CH$_3$)$_2$(CH$_2$)$_3$CH$_3$ | —(CH$_2$)$_3$CH$_3$ |
| 98  | —CH$_3$  | —CH$_3$  | —H | —C(CH$_3$)$_2$(CH$_2$)$_5$CH$_3$ | —(CH$_2$)$_3$CH$_3$ |
| 99  | —CH$_3$  | —CH$_3$  | —H | —C(CH$_3$)$_3$             | —(CH$_2$)$_7$CH$_3$ |
| 100 | —CH$_3$  | —CH$_3$  | —H | —C(CH$_3$)$_3$             | —CH$_2$CH$_3$ |
| 101 | —CH$_3$  | —CH$_3$  | —H | —C(CH$_3$)$_2$(CH$_2$)$_5$CH$_3$ | —CH$_2$CH$_3$ |
| 102 | —CH$_3$  | —CH$_3$  | —H | —(CH$_2$)$_3$CH$_3$           | —(CH$_2$)$_5$CH$_3$ |
| 103 | —CH$_3$  | —CH$_3$  | —H | —(CH$_2$)$_5$CH$_3$           | —(CH$_2$)$_5$CH$_3$ |

TABLE 8

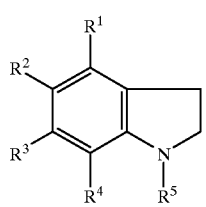

$R^2 = $ —NHCO—$R^6$

| Example | $R^1$ | $R^3$ | $R^4$ | $R^6$ | $R^5$ |
|---|---|---|---|---|---|
| 104 | —H | —OCH$_3$ | —H | —CH$_3$ | —CH$_2$CH$_3$ |
| 105 | —H | —OCH$_3$ | —H | —(CH$_2$)$_3$CH$_3$ | —CH$_2$CH$_3$ |
| 106 | —H | —OCH$_3$ | —H | —(CH$_2$)$_5$CH$_3$ | —CH$_2$CH$_3$ |

TABLE 8-continued

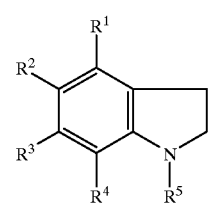

$R^2 = $ —NHCO—$R^6$

| Example | $R^1$ | $R^3$ | $R^4$ | $R^6$ | $R^5$ |
|---|---|---|---|---|---|
| 107 | —H | —OCH$_3$ | —H | —CH$_3$ | —(CH$_2$)$_3$CH$_3$ |
| 108 | —H | —OCH$_3$ | —H | —(CH$_2$)$_3$CH$_3$ | —(CH$_2$)$_3$CH$_3$ |

TABLE 9

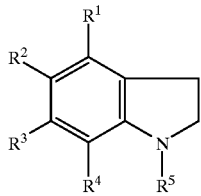

R⁴ = —NHCO—R⁶

| Example | R¹ | R² | R³ | R⁶ | R⁵ |
|---|---|---|---|---|---|
| 109 | —CH₃ | —H | —CH₃ | —C(CH₃)₃ | —(CH₂)₅CH₃ |
| 110 | —H | —H | —CH₃ | —C(CH₃)₃ | —(CH₂)₅CH₃ |
| 111 | —CH₃ | —H | —CH₃ | —C(CH₃)₂(CH₂)₈CH₃ | —(CH₂)₅CH₃ |
| 112 | —OCH₃ | —H | —OCH₃ | —C(CH₃)₃ | —(CH₂)₅CH₃ |
| 113 | —CH₃ | —H | —CH₃ | —C(CH₃)₃ | —(CH₂)₃CH₃ |
| 114 | —CH₃ | —H | —CH₃ | —C(CH₃)₂(CH₂)₃CH₃ | —(CH₂)₃CH₃ |
| 115 | —CH₃ | —H | —CH₃ | —C(CH₃)₂(CH₂)₅CH₃ | —(CH₂)₃CH₃ |
| 116 | —CH₃ | —H | —CH₃ | —C(CH₃)₃ | —(CH₂)₇CH₂ |
| 117 | —CH₃ | —H | —CH₃ | —C(CH₃)₃ | —CH₂CH₃ |
| 118 | —CH₃ | —H | —CH₃ | —C(CH₃)₂(CH₂)₅CH₃ | —CH₂CH₃ |

EXPERIMENTAL EXAMPLE 1

ACAT Inhibitor Activity

A high cholesterol feed [a feed added with cholesterol (1%), Clea Japan, Inc.] was fed to male Japanese white rabbits weighing 2–2.5 kg at 100 g per day and the rabbits were bred for 4 weeks. The rabbits were killed by bleeding under anesthesia and small intestine was removed. The mucous membrane of small intestine was peeled, collected and homogenated. The homogenate was centrifuged at 4° C. and 10,000 rpm for 15 min. The obtained supernatant was further centrifuged at 4° C. and 41,000 rpm for 30 minutes to give microsomal fractions. Using this microsomal suspension as an enzyme sample, dimethyl sulfoxide (DMSO, 5 μl) or a test compound dissolved in DMSO (test compound solution, 5 μl), and a reaction substrate [1-$^{14}$C]-oleoyl CoA were added to a reaction buffer. After incubation at 37° C. for 5 minutes, a chloroform- methanol mixture was added to stop the reaction. Water was added thereto and mixed, and chloroform layer was separated. The solvent was evaporated to dryness, and the residue was dissolved in hexane. The mixture was subjected to thin layer chromatography using a silica gel plate. The spots of cholesteryl oleate on the silica gel plate were scraped, and quantitatively assayed on a liquid scintillation counter. The ACAT inhibitory activity of the test compound was expressed as a proportion (%) of inhibition of cholesteryl oleate, namely, the proportion of inhibition of cholesteryl oleate production as compared to control.

The results are shown in Tables 10–11.

EXPERIMENTAL EXAMPLE 2

Serum Total Cholesterol Reducing Effect

Male Wister rats weighing 180–200 g were bred under free access to a high cholesterol feed [added with cholesterol (1%), cholic acid (0.5%) and coconut oil (10%), Clea Japan, Inc.] for 3 days, during which period a test compound (10–100 mg/kg) suspended in 5% gum arabic, solution was forcibly administered once a day orally for 3 days. Only 5% gum arabic solution was administered to control animals. After final administration, the test animals were fasted for 5 hours and the blood was taken. The serum total cholesterol level was determined using a commercially available assay kit (cholesterol-E-Test Wako, Wako Pure Chemical Industries, Ltd.). The activity of the test compound was expressed as a proportion (%) of reduction of serum total cholesterol level, namely, the proportion of reduction of serum total cholesterol as compared to control.

The results are shown in Tables 10–11.

EXPERIMENTAL EXAMPLE 3

LDL Peroxidation Inhibitory Effect

Male Japanese white rabbits weighing 2–2.5 kg were bred on 100 g per day of a high cholesterol feed [added with cholesterol (1%), Clea Japan, Inc.] for 4 weeks. The blood was taken from carotid and plasma was obtained. Then, LDL was fractionated from the plasma by ultracentrifugation, dialyzed for one day and preserved at 4° C. LDL (400 μg) and aqueous copper sulfate solution (final concentration 5 μM) were added to bufferized Ham F-10 medium (2 ml, GIBCO, USA). DMS0 or a solution (20 μl) of test compound dissolved in DMSO was added and the mixture was incubated at 37° C. for 24 hours. After the completion of the incubation, LDL peroxide in medium was allowed to develop color by thiobarbituric acid method and assayed as malondialdehyde. The activity of the test compound was expressed as malondialdehyde production inhibitory ratio (%), namely, the proportion of inhibition of production of malondialdehyde as compared to control.

The results are shown in Tables 10–11.

EXPERIMENTAL EXAMPLE 4

Plasma Lipoperoxidation Inhibitory Effect

The blood was taken from male Japanese white rabbits weighing 2–2.5 kg under anesthesia and heparinized plasma was separated by a conventional method. To the plasma (2.0 ml) was added DMSO or a solution (20 μl, final concentration 10$^{-5}$ M) of test compound dissolved in DMSO, and aqueous copper sulfate solution (final concentration 5 mM) was added immediately thereafter. The mixture was incubated at 37° C. for 3 hours. After the completion of the incubation, 20% trichloroacetic acid was added to stop the reaction. Then, the mixture was centrifuged at 4° C., 4,500 rpm for 15 minutes. The lipoperoxide in the supernatant thus obtained was assayed as malondialdehyde upon color development by thiobarbituric acid method. The activity of the test compound was expressed as malondialdehyde production inhibitory ratio (%), namely, the proportion of inhibition of production of malondialdehyde as compared to control.

The results are shown in Tables 10–11.

TABLE 10

| Test compound | Result of Exp. Ex. 1 (%) *1 | Result of Exp. Ex. 2 (%) *2 | Result of Exp. Ex. 3 (%) *3 | Result of Exp. Ex. 4 (%) *4 |
|---|---|---|---|---|
| Example 1 | 76.6 ** | 12.9 *** | 99.2 | 94.3 |
| Example 2 | 59.9 ** | — | 99.5 | 95.8 |
| Example 3 | 97.5 ** | 54.4 ** | 93.3 | 90.4 |
| Example 4 | 94.9 ** | 21.4 ** | 59.5 | 92.0 |
| Example 6 | 99.8 ** | 53.3 ** | 24.8 | 37.4 |
| Example 7 | 96.2 ** | 19.2 ** | 86.6 | 86.4 |
| Example 8 | 99.7 ** | 48.0 ** | 91.9 | 85.1 |
| Example 9 | 81.3 ** | 51.3 ** | 93.7 | 81.6 |
| Example 10 | 98.7 ** | 55.2 ** | 18.3 | 82.6 |
| Example 11 | 99.2 ** | 59.5 * | 91.6 | 78.8 |
| Example 12 | 71.9 ** | 30.3 ** | 90.3 | 74.9 |
| Example 13 | 96.0 ** | 28.4 ** | 82.4 | 87.1 |
| Example 14 | 96.6 ** | 53.9 ** | 88.3 | 93.1 |
| Example 15 | 93.1 ** | 35.0 * | 12.3 | 90.1 |
| Example 17 | 96.7 ** | 27.0 * | 89.6 | 91.1 |
| Example 18 | 69.6 * | 22.3 ** | 34.0 | 87.1 |
| Example 20 | 22.7 * | 7.8 * | 67.8 | 91.1 |
| Example 21 | 94.4 ** | 28.3 * | 92.1 | 91.4 |
| Example 22 | 78.5 ** | 38.6 *** | 40.6 | 92.8 |
| Example 23 | 88.8 ** | 23.6 ** | 54.8 | 90.5 |

*1: ACAT inhibition (concentration *: $10^{-4}$ M, **: $10^{-5}$ M)
*2: reduction of serum total cholesterol (dose *: 10 mg/kg/day, : 30 mg/kg/day, *: 100 mg/kg/day)
*3: LDL peroxidation inhibition (concentration : $10^{-5}$ M)
*4: plasma lipoperoxidation inhibition (concentration : $10^{-5}$ M)

TABLE 11

| Test compound | Result of Exp. Ex. 1 (%) *1 | Result of Exp. Ex. 2 (%) *2 | Result of Exp. Ex. 3 (%) *3 | Result of Exp. Ex. 4 (%) *4 |
|---|---|---|---|---|
| Example 24 | 97.1 ** | 28.3 ** | 42.2 | 90.5 |
| Example 25 | 96.8 ** | 50.5 ** | 92.2 | 93.1 |
| Example 26 | 26.5 ** | 37.4 ** | 43.3 | 90.1 |
| Example 27 | 95.5 ** | 56.9 *** | 92.2 | 91.1 |
| Example 28 | 79.4 ** | 20.8 *** | 92.2 | 91.1 |
| Example 29 | 86.6 ** | 6.9 ** | 91.9 | 91.1 |
| Example 30 | 83.0 ** | 25.7 *** | 94.1 | 91.8 |
| Example 31 | 93.8 ** | 49.0 ** | 90.3 | 90.8 |
| Example 32 | 93.9 ** | 57.4 ** | 85.3 | 89.1 |
| Example 33 | 82.2 ** | 7.2 ** | 87.0 | 89.5 |
| Example 34 | 91.0 ** | 50.2 ** | 82.9 | 89.8 |
| Example 35 | 84.6 ** | 20.8 ** | 71.9 | 91.4 |
| Example 36 | 95.9 ** | 50.2 ** | 83.2 | 89.1 |
| YM-750 | 92.3 ** | 43.8 ** | 0 | — |
| Probucol | 3.4 ** | 7.3 * | 89.4 | 87.5 |

*1: ACAT inhibition (concentration *: $10^{-4}$ M, **: $10^{-5}$ M)
*2: reduction of serum total cholesterol (dose *: 10 mg/kg/day, : 30 mg/kg/day, *: 100 mg/kg/day)
*3: LDL peroxidation inhibition (concentration : $10^{-5}$ M)
*4: plasma lipoperoxidation inhibition (concentration : $10^{-5}$ M)
YM-750: 1-cycloheptyl-1-[(2-fluorenyl)methyl]-3-(2,4,6-trimethyl-phenyl)urea
Probucol: 4,4'-isopropylidenedithiobis(2,6-di-t-butylphenol)

FORMULATION EXAMPLE 1

Tablets having the following composition are prepared by a coventional method.

| Compound of Example 3 | 25 mg |
| Polyvinylpyrrolidone | 20 mg |
| Starch | 75 mg |
| Magnesium stearate | 2 mg |

FORMULATION EXAMPLE 2

Capsules having the following composition are prepared by a conventional capsule packing method.

| Compound of Example 6 | 100 mg |
| Lactose | 25 mg |
| Magnesium stearate | 1 mg |

The heterocyclic derivative and pharmaceutically acceptable salts thereof of the present invention show superior ACAT inhibitory activity and lipoperoxidation inhibitory activity, and are useful as ACAT inhibitors or hyperlipemia inhibitors. To be specific, they are useful for the prevention and treatment of arteriosclerotic lesions such as arteriosclerosis, hyperlipemia and diabetes, as well as ischemic diseases of brain, heart and the like.

What is claimed is:

1. A method for inhibiting lipoperoxidation in a host for the prophylaxis or treatment of arteriosclerosis, diabetes, hyperlipemia, or cerebrovascular or cardiovascular ischemic diseases in said host comprising contacting said host with a heterocyclic compound of the formula (I)

(I)

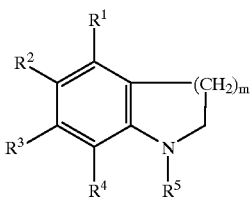

wherein
one of $R^1$, $R^2$, $R^3$, and $R^4$ is a group of the formula —NHCO—$R^6$
wherein $R^6$ is selected from the group consisting of $C_1$–$C_{12}$ alkyl, cyclo $C_3$–$C_6$ alkyl, cyclo $C_3$–$C_6$ alkyl $C_1$–$C_3$ alkyl, phenyl, naphthyl, phenyl $C_1$–$C_4$ alkyl, naphthyl $C_1$–$C_4$ alkyl, pyrrolidinyl, piperidyl, piperidino, morpholinyl, morpholino, piperazinyl, pyrrolyl, imidazolyl, pyridyl, pyrrolidinyl $C_1$–$C_8$ alkyl, piperidyl $C_1$–$C_8$ alkyl, piperidino $C_1$–$C_8$ alkyl, morpholinyl $C_1$–$C_8$ alkyl, morpholino $C_1$–$C_8$ alkyl, piperazinyl $C_1$–$C_8$ alkyl, pyrrolyl $C_1$–$C_8$ alkyl, imidazolyl $C_1$–$C_8$ alkyl, and pyridyl $C_1$–$C_8$ alkyl (wherein any of the foregoing is optionally substituted with a $C_1$–$C_4$ alkyl, amino, hydroxy, di($C_1$–$C_4$) alkylamino, $C_1$–$C_4$ aminoalkyl, $C_1$–$C_4$ alkoxy, carboxyl, $C_1$–$C_4$ alkoxycarbonyl, $C_1$–$C_4$ carboxyalkyl, $C_2$–$C_5$ acyloxy, phenyl, phenoxy, halogen, ($C_1$–$C_4$)alkyl phenyl($C_1$–$C_4$)alkylamino, or di[phenyl($C_1$–$C_4$)alkyl]amino), —$R^A SO_3 A$, and —$R^B PO_3 B$ where $R^A$ and $R^B$ are each $C_1$–$C_8$ alkylene and A and B are each alkali metal or hydrogen atom, —$NR^7R^8$ where $R^7$ is selected from the group consisting of $C_1$–$C_{12}$ alkyl, cyclo $C_3$–$C_6$ alkyl, cyclo $C_3$–$C_6$ alkyl $C_1$–$C_3$ alkyl, phenyl, naphthyl, phenyl $C_1$–$C_4$ alkyl, and naphthyl $C_1$–$C_4$ alkyl (wherein any of the foregoing is optionally substituted with a $C_1$–$C_4$ alkyl, amino, hydroxy, di($C_1$–$C_4$)alkylamino, $C_1$–$C_4$ aminoalkyl, $C_1$–$C_4$ alkoxy, carboxyl, $C_1$–$C_4$ alkoxycarbonyl, $C_1$–$C_4$ carboxyalkyl, $C_2$–$C_5$ acyloxy, phenyl, phenoxy, halogen, ($C_1$–$C_4$)alkyl phenyl($C_1$–$C_4$)alkylamino, or di[phenyl($C_1$–$C_4$)alkyl]amino), and $R^8$ is hydrogen atom or $C_1$–$C_4$ alkyl, and —$R^9$—$OCOR^{10}$ where $R^9$ is $C_1$–$C_8$ alkylene and $R^{10}$ is selected from the group consisting of $C_1$–$C_{12}$ alkyl, pyrrolidinyl, piperidyl, piperidino, morpholinyl, morpholino, piperazinyl, pyrrolyl, imidazolyl, pyridyl, pyrrolidinyl $C_1$–$C_8$ alkyl, piperidyl $C_1$–$C_8$ alkyl, piperidino $C_1$–$C_8$ alkyl, morpholinyl $C_1$–$C_8$ alkyl, morpholino $C_1$–$C_8$ alkyl, piperazinyl $C_1$–$C_8$ alkyl, pyrrolyl $C_1$–$C_8$ alkyl, imidazolyl $C_1$–$C_8$ alkyl, and pyridyl $C_1$–$C_8$ alkyl (wherein any of the foregoing is optionally substituted with a $C_1$–$C_4$ alkyl, amino, hydroxy, $C_1$–$C_4$ dialkylamino, $C_1$–$C_4$ aminoalkyl, $C_1$–$C_4$ alkoxy, carboxyl, $C_1$–$C_4$ alkoxycarbonyl, $C_1$–$C_4$ carboxyalkyl, $C_2$–$C_5$ acyloxy, phenyl, phenoxy, halogen, ($C_1$–$C_4$)alkyl phenyl ($C_1$–$C_4$)alkylamino, or di[phenyl($C_1$–$C_4$)alkyl]amino), and the remaining three of $R^1$, $R^2$, $R^3$, or $R^4$ may be the same or different and each is independently a hydrogen atom, a $C_1$–$C_4$ alkyl or a $C_1$–$C_4$ alkoxy;

$R^5$ is selected from the group consisting of $C_1$–$C_{12}$ alkyl, cyclo $C_3$–$C_6$ alkyl, cyclo $C_3$–$C_6$ alkyl $C_1$–$C_3$ alkyl, phenyl, naphthyl, phenyl $C_1$–$C_4$ alkyl, naphthyl $C_1$–$C_4$ alkyl, pyrrolidinyl, piperidyl, piperidino, morpholinyl, morpholino, piperazinyl, pyrrolyl, imidazolyl, pyridyl, pyrrolidinyl $C_1$–$C_8$ alkyl, piperidyl $C_1$–$C_8$ alkyl, piperidino $C_1$–$C_8$ alkyl, morpholinyl $C_1$–$C_8$ alkyl, morpholino $C_1$–$C_8$ alkyl, piperazinyl $C_1$–$C_8$ alkyl, pyrrolyl $C_1$–$C_8$ alkyl, imidazolyl $C_1$–$C_8$ alkyl, and pyridyl $C_1$–$C_8$ alkyl (wherein any of the foregoing is optionally substituted with a $C_1$–$C_4$ allyl, amino, hydroxy, $C_1$–$C_4$ dialkylamino, $C_1$–$C_4$ aminoalkyl, $C_1$–$C_4$ alkoxy, carboxyl, $C_1$–$C_4$ alkoxycarbonyl, $C_1$–$C_4$ carboxyalkyl, $C_2$–$C_5$ acyloxy, phenyl, phenoxy, halogen, ($C_1$–$C_4$) alkyl phenyl($C_1$–$C_4$)alkylamino, or di[phenyl($C_1$–$C_4$) alkyl]amino), $C_2$–$C_5$ alkenyl, $C_2$–$C_8$ alkynyl, a and di($C_1$–$C_8$ )alkylamino($C_2$–$C_8$)acyloxy($C_1$–$C_8$ )alkyl, —$R^DSO_3D$ —$R^EPO_3E$ where $R^D$ and $R^E$ are each $C_1$–$C_8$ alkylene and D and E are each alkali metal or hydrogen atom, and m is 1, or a pharmaceutically acceptable salt thereof, with the proviso that $R^5$ is not ethyl when $R^1$, $R^3$, and $R^4$ are hydrogen atom, $R^2$ is (4-methylpentanoyl)amino, and m is 1.

2. The method of claim 1, wherein one of $R^2$ and $R^4$ is NHCO—$R^6$, and the other is hydrogen; $R^1$ and $R^3$ are both $C_1$–$C_4$ alkyl or both $C_1$–$C_4$ alkoxy; (when $R^5$ is unsubstituted $C_1$–$C_{12}$ alkyl, $R^6$ is $C_1$–$C_{12}$ alkyl (which is optionally substituted with hydroxy, $C_2$–$C_5$ acyloxy, or $C_1$–$C_4$ alkoxy), pyrrolidinyl, piperidyl, piperidino, morpholinyl, morpholino, piperazinyl, pyrrolyl, imidazolyl, pyridyl, pyrrolidinyl $C_1$–$C_8$ alkyl, piperidyl $C_1$–$C_8$ alkyl, piperidino $C_1$–$C_8$ alkyl, morpholinyl $C_1$–$C_8$ alkyl, morpholino $C_1$–$C_8$ alkyl, piperazinyl $C_1$–$C_8$ alkyl, pyrrolyl $C_1$–$C_8$ alkyl, imidazolyl $C_1$–$C_8$ alkyl, pyridyl $C_1$–$C_8$ alkyl, —$NR^7R^8$ (wherein $R^7$ is hydrogen, and $R^8$ is $C_1$–$C_{12}$ alkyl), or —$R^9$—$OCOR^{10}$ (wherein $R^9$ is $C_1$–$C_8$ alkylene and $R^{10}$ is pyrrolidinyl, piperidyl, piperidino, morpholinyl, morpholino, piperazinyl, pyrrolyl, imidazolyl, or pyridyl) and m is 1, and when $R^5$ is $C_1$–$C_{12}$ alkyl, which is substituted by $C_2$–$C_5$ acyloxy or $C_1$–$C_4$ alkoxy, $R^6$ is unsubstituted $C_1$–$C_{12}$ alkyl and m is 1, or a pharmaceutically acceptable salt thereof.

* * * * *

UNITED STATES PATENT AND TRADEMARK OFFICE
CERTIFICATE OF CORRECTION

PATENT NO. : 6,414,012 B1
DATED : July 2, 2002
INVENTOR(S) : Matsui et al.

It is certified that error appears in the above-identified patent and that said Letters Patent is hereby corrected as shown below:

<u>Title page,</u>
Item [56], FOREIGN PATENT DOCUMENTS, second column, first reference:
"WO   WO 94/14801   7/1994" should read as -- WO   94/14801   7/1994 --.
Second column, second reference: "WO   WO   97/12860   4/1997" should read as
-- WO   97/12860   4/1997 --.
OTHER PUBLICATIONS,
"1-Act-5-Bromoindoline," should read as -- 1-Acyl-5-Bromoindoline --

<u>Column 32,</u>
Line 3, "allyl" should read -- alkyl --.
Line 8, "$C_2$-$C_5$ alkenyl," should read -- $C_2$-$C_8$ alkenyl, --.
Line 8, "a and" should read -- a --.
Line 9, "di($C_1$-$C_8$ )alkylamino($C_2$-$C_8$)acyloxy($C_1$-$C_8$ )alkyl," should read -- di($C_1$-$C_8$) alkylamino($C_2$-$C_5$)acyloxy($C_1$-$C_8$)alkyl, --.
Line 10, "—$R^D SO_3 D$ —$R^E PO_3 E$" should read -- —$R^D SO_3 D$ and —$R^E PO_3 E$ --.
Line 18, "alkoxy; (when" should read -- alkoxy; when --.

Signed and Sealed this

Thirty-first Day of December, 2002

JAMES E. ROGAN
*Director of the United States Patent and Trademark Office*